United States Patent
Ross et al.

(10) Patent No.: US 10,198,928 B1
(45) Date of Patent: Feb. 5, 2019

(54) FALL DETECTION SYSTEM

(71) Applicant: MedHab, LLC, Mansfield, TX (US)

(72) Inventors: Johnny Ross, Mansfield, TX (US); Simon Joakim Olsen, Karmsund (NO); Donna Caroline Samuelson, San Angelo, TX (US); Mathew Aaron Gray, San Angelo, TX (US)

(73) Assignee: MEDHAB, LLC., Mansfield, TX (US)

( * ) Notice: Subject to any disclaimer, the term of this patent is extended or adjusted under 35 U.S.C. 154(b) by 0 days.

(21) Appl. No.: 15/858,930

(22) Filed: Dec. 29, 2017

(51) Int. Cl.
*G08B 21/04* (2006.01)
*A61B 5/11* (2006.01)

(52) U.S. Cl.
CPC ........ *G08B 21/0446* (2013.01); *A61B 5/1117* (2013.01); *A61B 2562/0219* (2013.01); *G08B 21/043* (2013.01)

(58) Field of Classification Search
CPC ..... A61B 5/002; A61B 5/1117; A61B 5/0024; A61B 5/1118; A61B 5/112; A61B 5/02438; A61B 5/1123; G08B 21/0446; G08B 21/0453
See application file for complete search history.

(56) References Cited

U.S. PATENT DOCUMENTS

| | | | |
|---|---|---|---|
| 6,160,478 A | 12/2000 | Jacobsen | |
| 6,201,476 B1 | 3/2001 | Depeursinge et al. | |
| 8,106,782 B2 | 1/2012 | Fredriksson et al. | |
| 8,217,795 B2 | 7/2012 | Carlton-Foss | |
| 8,408,041 B2 | 4/2013 | Kate et al. | |
| 8,614,630 B2 | 12/2013 | Narasimhan et al. | |
| 8,665,097 B2 | 3/2014 | Worthington et al. | |
| 8,814,811 B2 | 8/2014 | Scholten et al. | |
| 9,202,283 B2 | 1/2015 | Ramzi | |
| 8,952,818 B1 | 2/2015 | Zhang | |
| 9,005,141 B1 | 4/2015 | Najafi et al. | |
| 9,202,361 B2 | 12/2015 | Rubio Andres et al. | |
| 9,402,568 B2 | 8/2016 | Barfiled | |
| 9,588,135 B1 | 3/2017 | Narasimhan | |

(Continued)

FOREIGN PATENT DOCUMENTS

WO    WO 2010108287    9/2010

OTHER PUBLICATIONS

Author: Wilamowski, Cotton, Kaynak and Dundar; Title: Computing Gradient Vector and Jacobian Matrix in Arbitrarily Connected Neural Networks; IEEE Transacations on Industrial Electronics, vol. 55, No. 10; Date: Oct. 2008.

(Continued)

*Primary Examiner* — Mirza F Alam
(74) *Attorney, Agent, or Firm* — Eric Karich; Karich & Associates

(57) ABSTRACT

A system used to detect a fall and to provide data has a wearable device that includes a pre-filter, an accelerometer and a transmitter. The pre-filter includes buffers, a low pass filter, a flag, and a measuring device. The pre-filter receives data points transmitted by the accelerometer. The pre-filter generates a magnitude value, and calculates a jerk value in relation to the magnitude value. The pre-filter appends the jerk value to one of the buffers and provides the jerk value to the measuring device. The pre-filter further transmits the magnitude value to a neural network.

14 Claims, 9 Drawing Sheets

(56) References Cited

U.S. PATENT DOCUMENTS

| | | | |
|---|---|---|---|
| 2005/0240086 A1* | 10/2005 | Akay | A61B 5/0002 600/300 |
| 2006/0270949 A1* | 11/2006 | Mathie | A61B 5/0002 600/595 |
| 2006/0282021 A1 | 12/2006 | Devaul | |
| 2008/0129518 A1* | 6/2008 | Carlton-Foss | A61B 5/1117 340/573.1 |
| 2010/0121226 A1* | 5/2010 | Ten Kate | A61B 5/1117 600/595 |
| 2011/0045795 A1 | 2/2011 | Sacknoff | |
| 2012/0302200 A1 | 11/2012 | Esbensen | |
| 2013/0135097 A1 | 5/2013 | Doezema | |
| 2014/0276238 A1 | 9/2014 | Osorio | |
| 2015/0164377 A1* | 6/2015 | Nathan | A61B 5/1122 600/595 |
| 2016/0162781 A1 | 6/2016 | Lillicrap et al. | |
| 2016/0227361 A1 | 8/2016 | Booth et al. | |
| 2017/0169689 A1 | 6/2017 | Vagelos | |
| 2017/0172465 A1* | 6/2017 | Osorio | A61B 5/0205 |
| 2017/0188895 A1* | 7/2017 | Nathan | A61B 5/1122 |

OTHER PUBLICATIONS

Author: Wilamowski, Cotton, Kaynak and Dundar; Title: Method of Computing Gradient Vector and Jacobean Matrix in Arbitrarily Connected Neural Networks; Electrical and Computer Engineering, Auburn University, Auburn, Alabama; Date: 2009.

* cited by examiner

FALL DETECTION SYSTEM

BACKGROUND OF THE INVENTION

Field of the Invention

This invention relates generally to personal monitoring systems, and more particularly to efficient fall detection systems that track and filter a person's movements and provide data for detecting if the person has fallen and may have been injured.

Description of Related Art

Various care systems exist for monitoring a person's movements. Some systems monitor the movements of the elderly and persons with medical conditions; and such monitoring allows for timely interventions by those who are responsible for diagnosing, caring, rescuing, treating, or otherwise assisting such individuals. There are also many systems for monitoring young and uninjured persons, for tracking daily habits, activity levels, and similar data (e.g., steps taken during the day, calories burned, hours of sleep, etc.). Examples of prior art systems are as follows:

Devaul, U.S. 2006/0282021, teaches a motion analysis telemonitor system that includes a wearable monitoring device that monitors the activity level and movements of a person wearing the device. The wearable monitoring device is used to track fire-fighters, and is able to determine whether the person has fallen through a model analysis technique using characteristic movements of a fall. The wearable device generally transmits data and alerts over a short distance to a console. The console, in turn, transmits data and alerts to a monitoring center. The motion analysis telemonitor system is also able to monitor progression of a disease through changes in movement, which can indicate fatigue.

Devaul teaches the use of "Bayes Theorem" to assist in determining classification of any movement into a model, to assist in determining whether a movement is a fall (or similar situation) or regular movement. This system also includes ancillary components, such as a GPS system, a dead reckoning system, and other components, and may be used in conjunction with a cell phone or similar electronics device.

Jacobsen, U.S. Pat. No. 6,160,478, teaches a health monitoring system for monitoring the elderly which uses wristbands having accelerometers. The system looks for "spikes" in movement that may indicate a fall, especially if followed by a period of the person remaining prone and/or not moving. The system alerts caregivers in the event of a fall.

Carlton-Foss, U.S. Pat. No. 8,217,795, teaches a fall detection system that includes a wearable monitoring device that monitors the movement of a person, and may be worn on the wrist or other suitable location. The device monitors a sensor (e.g., accelerometer) and detects variation from the normal range and duration thereof. The system determines whether the wearer has fallen through an algorithmic analysis technique using parameters to evaluate the accelerations and timings of the events that comprise a fall. If the combination of the timing and variations from the normal ranges are sufficient as compared to preset thresholds, a fall report will be generated. The wearable device optionally allows qualified professionals to adjust or customize the parameters to optimize the evaluation to the requirements of particular users or classes of users. The wearable device generally transmits data and alerts over a short distance to a console or over a long distance using a connection to a long-distance back haul communication system such as cell network or internet or both. The device thus transmits data and alerts to a call center or other designated location.

Zhang, U.S. Pat. No. 8,952,818, teaches a wearable fall detection device configured for monitoring a wearer of the device. The device comprises a first sensor configured to generate elevation data that represents an elevation of the device, and a second sensor configured to generate acceleration data that represents a magnitude of acceleration of the device. The device also includes a processor configured to determine, based on the elevation data, an elevation of a floor located underneath the wearer, and detect a fall affecting the wearer. Detecting a fall may be done by determining that the acceleration data satisfies a fall hypothesis condition, and determining, based on the elevation data, that the apparatus is vertically displaced from the floor by less than a threshold distance.

Doezema, U.S. 2013/0135097, teaches a wearable, hands-free emergency alert device that responds automatically to a measurable physical effect of a fall event by the wearer to send an alert signal to a remote responder. The wearable device may be a bracelet with a flex circuit including an accelerometer; a manual alert to signal non-fall emergencies; a microphone and/or audio chip for voice communications between the user of the wearable device and a remote responder; one or more charging contacts so as to allow for induction and/or wireless charging of the device; and a wireless transmitter capable of sending a wireless alert signal in response to a sensed fall and capable of generating a response signal in response to receipt of a ping signal which may be used to determine the device's location.

Luo, W.O. 2010108287, teaches a wearable intelligent healthcare system for monitoring a subject and providing feedback from physiological sensors, activity sensors, a processor, a real-time detection and analyzing module for continuous health and activity monitoring, adjustable user setting mode with the adaptive optimization, data-collecting capability to record important health information, audio outputs to the user through audio path and audio interface, preset and user confirmable alarm conditions via wireless communications network to the appropriate individual for prompt and necessary assistance. The system uses noninvasive monitoring technology for continuous, painless and bloodless health state monitoring. The system works through the short range wireless link with carry-on mobile unit for displaying health information, making urgent contact to support center, doctor or individual, and for information transmission with a healthcare center.

While the prior art teaches various related systems and method, the prior art fails to teach a system and method with the novel and non-obvious elements and improvements that are claimed in the present application.

SUMMARY OF THE INVENTION

The present invention teaches certain benefits in construction and use which give rise to the objectives described below.

One embodiment of the present disclosure includes a computer-implemented method for providing data to a neural network for detecting a fall of a person having a portable electronic device. A data point is received at a pre-filter, where the pre-filter includes a first buffer, a second buffer, a low pass filter, and a measuring device. The pre-filter calculates a first magnitude value in view of the data point. The pre-filter passes the first magnitude value to the low pass filter to generate a second magnitude value. The pre-filter calculates a jerk value in relation to the second magnitude value and a third magnitude value. The third magnitude value is a magnitude value appended to the first buffer. The pre-filter appends the jerk value to the second buffer. The pre-filter also appends the second magnitude value to the first buffer. The pre-filter provides the jerk value to the measuring device. The pre-filter transmits the second magnitude value to the neural network. Other embodiments of this aspect include corresponding computer systems, apparatus, and computer programs recorded on one or more computer storage devices, each configured to perform the actions of the methods.

In an implementation, the pre-filter includes a flag and the measuring device includes a high threshold detector. The pre-filter sets the flag in response to the high threshold detector detecting the jerk value meeting a high threshold. The high threshold is greater than or equal to a high threshold value.

In an implementation, the pre-filter includes a flag and the measuring device includes a low threshold detector. When the flag is set, the pre-filter: passes the jerk value to the low threshold detector; detects the jerk value meeting a low threshold; and transmits the second magnitude value to the neural network in response to the detection of the jerk value meeting the low threshold. The low threshold is lower than a low threshold value.

In an implementation, the pre-filter includes a flag and in response the flag being set, meeting of a low threshold not being detected, and in response to greater than a predetermined number of data points being passed to the pre-filter since the flag was set, the pre-filter unsets the flag.

In an implementation, the third magnitude value is a last magnitude value appended to the first buffer.

One embodiment of the present disclosure includes a system for providing data to a neural network. A wearable device includes a pre-filter, an accelerometer, and a transmitter configured to communicate with a portable electronic device. The pre-filter includes a first buffer, a second buffer, a low pass filter, and a measuring device. The pre-filter is configured to receive one or more data points transmitted by the accelerometer, calculate a first magnitude value in view of the data point, and pass the first magnitude value to the low pass filter to generate a second magnitude value. The pre-filter is further configured to calculate a jerk value in relation to the second magnitude value and a third magnitude value. The third magnitude value is a magnitude value appended to the first buffer. The pre-filter is further configured to append the jerk value to the second buffer, append the second magnitude value to the first buffer, provide the jerk value to the measuring device, and transmit the second magnitude value to the neural network.

In an implementation, the pre-filter includes a flag and the measuring device includes a high threshold detector. The pre-filter is configured to set the flag in response to the high threshold detector detecting the jerk value meeting a high threshold. The high threshold is greater than or equal to a high threshold value.

In an implementation, the pre-filter includes a flag. The measuring device includes a low threshold detector and when the flag is set, the pre-filter is configured to: pass the jerk value to the low threshold detector, detect the jerk value meeting a low threshold, and transmit the second magnitude value to the neural network in response to detecting of the jerk value meeting the low threshold. The low threshold is lower than a low threshold value.

In an implementation, the pre-filter sets the flag.

In an implementation, the pre-filter is configured to unset the flag in response to: the low threshold detector not detecting the jerk value meeting the low threshold; and a predetermined number of data points being passed to the pre-filter since the flag was set.

One embodiment of the present disclosure includes a wearable device system that includes a pre-filter, an accelerometer, and a transmitter. The transmitter is configured to communicate with a portable electronic device. The pre-filter includes a first buffer, a second buffer, a low pass filter, a flag, and a low threshold detector. The pre-filter is configured to receive one or more data points transmitted by the accelerometer, calculate a first magnitude value in view of a data point, and pass the first magnitude value to the low pass filter to generate a second magnitude value. The pre-filter is further configured to calculate a jerk value in relation to the second magnitude value and a third magnitude value. The third magnitude value is a magnitude value appended to the first buffer. The pre-filter is further configured to append the jerk value to the second buffer, append the second magnitude value to the first buffer, provide the jerk value to the low threshold detector in response to the flag being set, and provide the second magnitude value to the transmitter in response to the low threshold detector detecting the jerk value meeting a low threshold. The low threshold lower is a low threshold value.

In an implementation, the pre-filter further includes a high threshold detector. The pre-filter is configured to: set the flag in response to the high threshold detector detecting the jerk value meeting a high threshold. The high threshold is greater than or equal to a high threshold value.

In an implementation, the pre-filter sets the flag.

In an implementation, the pre-filter is configured to unset the flag in response to: the low threshold detector not detecting the jerk value meeting the low threshold; and a predetermined number of data points being passed to the pre-filter since the flag was set.

Implementations of the described techniques may include hardware, a method or process, or computer software on a computer-accessible medium.

A primary objective of the present invention is to provide an efficient fall detection system having advantages not taught by the prior art.

Another objective is to provide an efficient fall detection system that is able to provide data to reliably detect a fall of a user or to train a neural network accordingly.

Another objective is to provide a fall detection system that does not utilize a large amount of data in order to train the neural network and/or reliably detect a fall.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The advantages and features of the present invention will become better understood with reference to the following more detailed description taken in conjunction with the accompanying drawings in which.

DETAILED DESCRIPTION OF THE INVENTION

Figure 1:
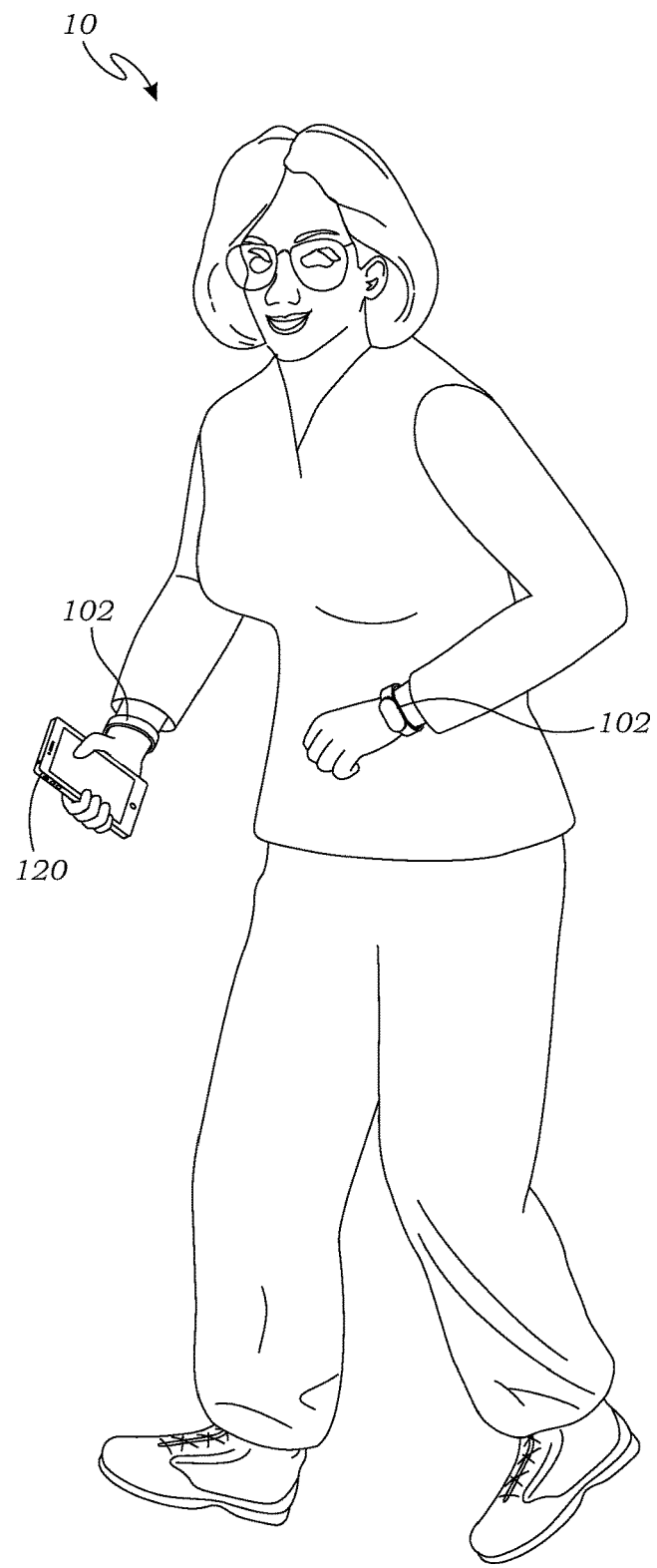
FIG. 1 is a perspective view of a user using a fall detection system of the present invention, in this embodiment wearing two wearable sensor devices and carrying a portable electronic device.

FIG. 1 is a perspective view of a user using a fall detection system 10, in this embodiment wearing wearable sensor devices 102, in this embodiment in the form of wrist bands worn on each of the user's wrists. The user is also carrying a portable electronic device 120, which in this case is in the form of a smart phone.

First, the user is monitored at all times for the purposes of detecting falls and other traumatic events that may require urgent medical care. The details of this process are described in greater detail below.

Second, the user is monitored for detecting, monitoring, and reporting physical activities. The user is monitored while performing a set of predefined physical activities, which, for example, may be prescribed by a health practitioner or a fitness trainer. For example, an elderly woman may perform various exercises prescribed by a doctor for routine body movement and healthy lifestyle. During such exercises, the elderly woman may wear one or more of the sensor devices 102-1 and 102-2 (collectively, wearable sensor devices 102) for being monitored to ensure adherence to the prescribed exercise schedule and inform caregivers or rescuers in case of falling during the exercises. The wearable sensor devices 102 may operate in communication with the portable electronic device 120 to track the user, detect if the user has fallen, and report any deviation from the prescribed set of physical activity or falling of the user.

Figure 2:
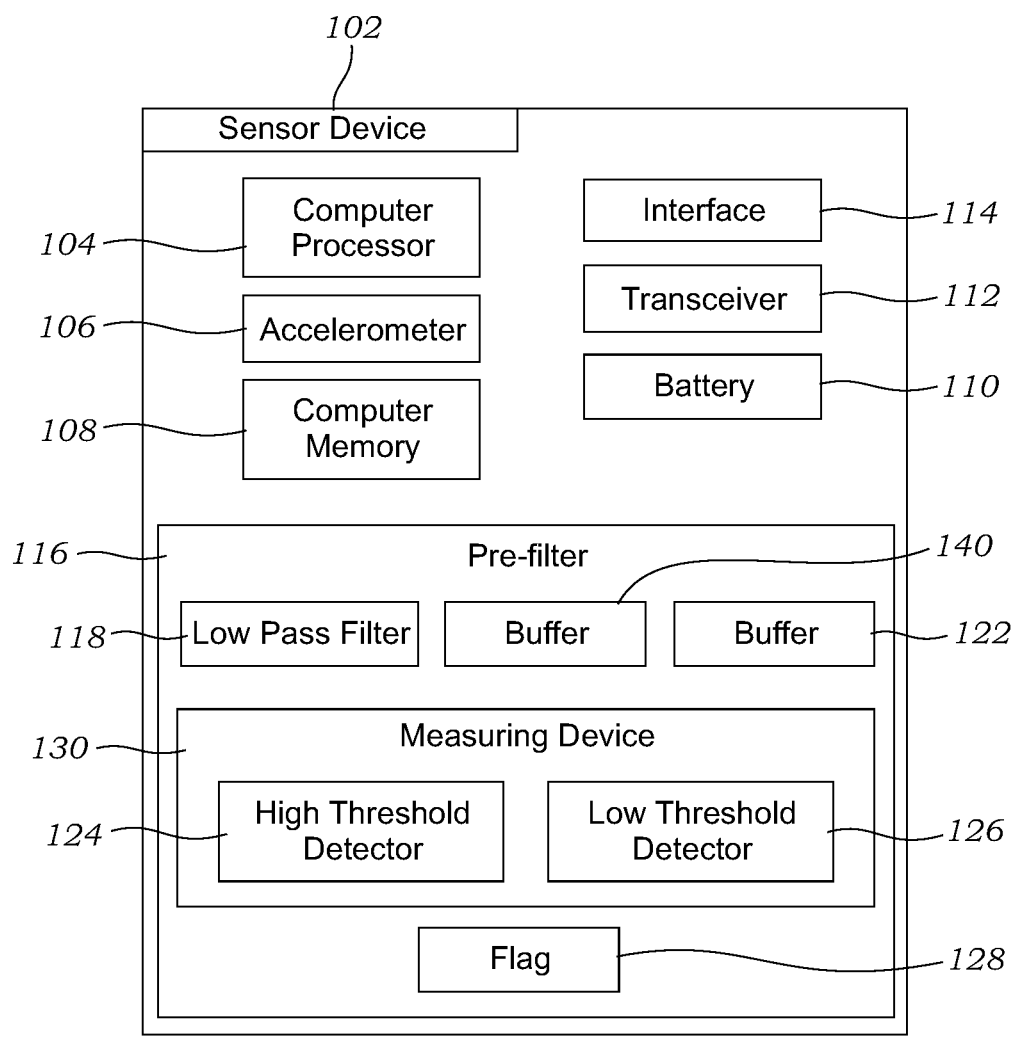
FIG. 2 is a block diagram of operable components of one of the wearable sensor devices of FIG. 1, according to one embodiment of the present invention.

FIG. 2 is a block diagram that illustrates electronic components of the wearable sensor devices 102. As illustrated in FIG. 2, the wearable sensor device 102 may be appropriately shaped and adapted into any wearable device (e.g., a wrist band, arm band, head band, belt, article of clothing, etc.). In one embodiment, the wearable sensor devices 102-1 includes a printed circuit board ("PCB") (not shown) having or being operably attached to a computer processor 104, a computer memory 108, and a battery 110.

Each of the components may be operably connected to the processor 104 by electrical connectors or any other operative connection known in the art, related art, or developed later. The processor 104 and the memory 108 may be any form of processor or processors, memory chip(s) or devices, microcontroller(s), and/or any other devices known in the art, related art, or developed later.

The battery 110 supplies power to the processor 104. The battery 110 may be rechargeable which can be charged by an external power source, or in alternative embodiments it may be replaceable. The wearable sensor devices 102 may further include an inductive charging coil (not shown) which may be operably mounted adjacent the battery 110 and/or the PCB. The inductive charging coil is used to charge the battery 110 by using an external inductive charger (not shown). Other devices or systems known in the art for supplying power may also be utilized, including various forms of charging the battery 110, and/or generating power directly using piezoelectric, solar, or other devices.

The wearable sensor devices 102 may further include one or more accelerometers 106, one or more micro-electro-mechanical-systems "MEMS" gyroscopes (not shown), and/or a compass (not shown) to record movement, rotation, and direction data respectively and supply the data to the processor 104. The accelerometer 106, the gyroscope (not shown), and the compass (not shown) may be operably connected to the processor 104 via being operably mounted on the PCB, or they may be mounted elsewhere and connected via the wires. In view of the present embodiment, the gyroscope and the compass are optional.

The integrated motion tracker including the accelerometer 106 provides data on the linear acceleration in three linear dimensions, roll, pitch, yaw, position, bearing, and heading. These nine coordinate measurements provide a complete description of the motion and position of the user. Other motion trackers may also be used by those skilled in the art and are within the scope of the present invention.

The processor 104 may also include the memory to store data collected by the accelerometer 106, and a transceiver 112 to transmit and receive signals for communication between the processor 104 and external computing devices enabled to send and receive the signals. The processor 104, the memory 108, and the transceiver 112 may all be mounted on the PCB, or in other suitable locations as determined by one ordinarily skilled in the art. The transceiver 112 may communicate via local communications protocols such as Bluetooth®, cellular networks, WIFI, and/or any other communications standards known in the art. An interface 114 (i.e., a graphical user interface) may also be included to display textual and/or video data.

Figure 4:
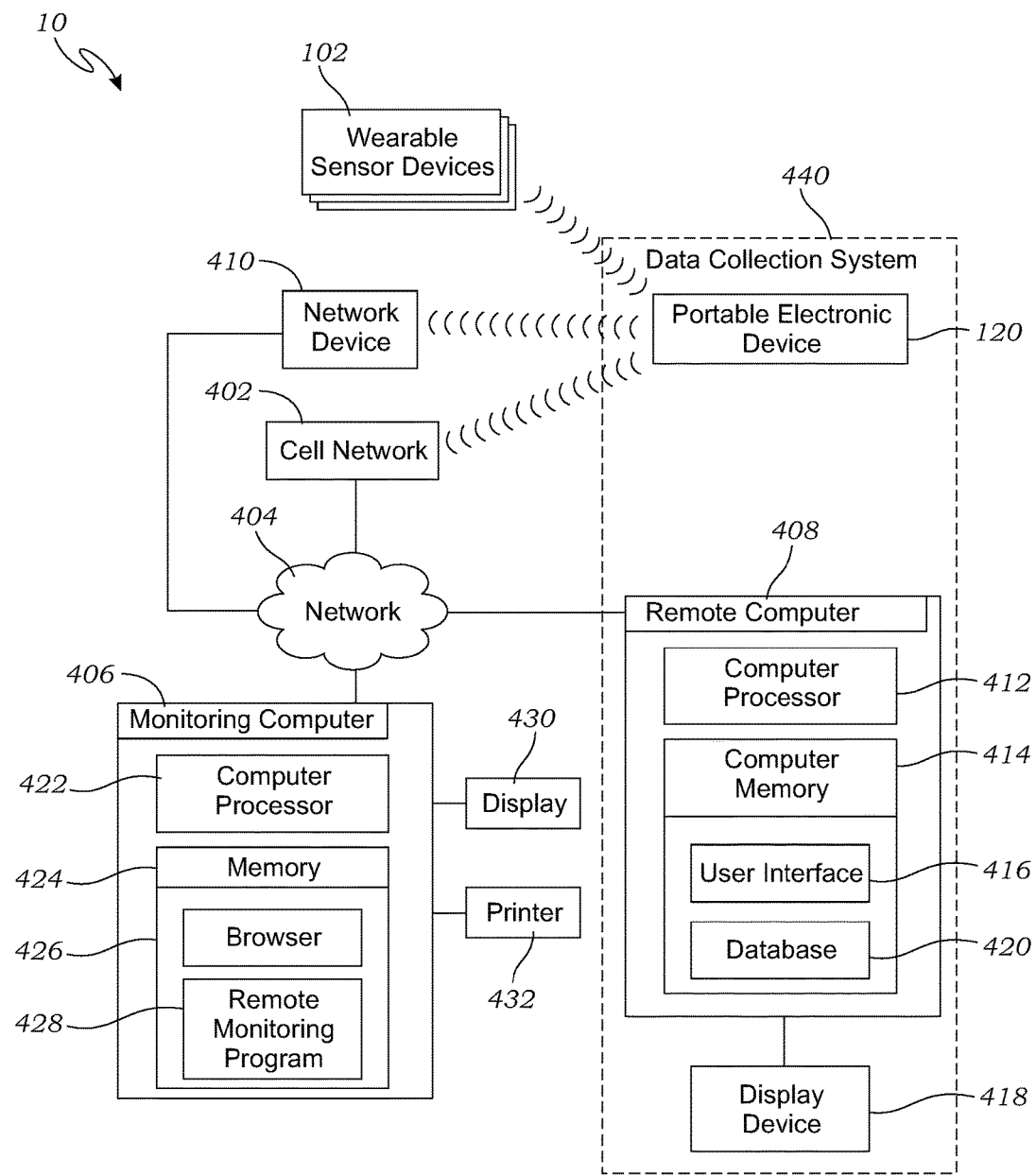
FIG. 4 is a block diagram of one embodiment of an exemplary personal monitoring system that includes the portable electronic device, a monitoring computer, and a remote computer for monitoring the personal monitoring system and storing data, according to one embodiment of the present invention.

As the user wearing the wearable sensor devices 102 performs a physical activity (e.g., running, walking, climbing stairs, sitting, jogging, routine or prescribed exercises, push-ups, sit-ups, cycling, etc.), acceleration data from the accelerometer 106 may be collected by the processor 104 for use in a variety of ways. The data may correspond to any change in acceleration of the wearable sensor devices 102 across X, Y, and Z axes with respect to the gravity of earth due to the physical activity being performed by the user. The wearable sensor devices 102 may use the transceiver 112 to connect and transfer data from the wearable sensor devices 102 to a local computer (e.g., the portable electronic device 120) and/or remote computer (408, as shown in FIG. 4), and/or monitoring computer (406, as shown in FIG. 4). The data may be transmitted by the transceiver 112, which is defined to include any device known to those ordinarily skilled in the art that are functional for this purpose. In particular, the data may be transferred in packets or bundles, containing multiple bytes or bits of information. The bundling of the data may be performed according to those ordinarily skilled in the art for optimizing the data transfer rate between the wearable sensor devices 102 and any remote receiver. Alternatively, in another embodiment, the data may be reported via a separate reporting device (not shown) worn by the user, located nearby, or located remotely. In another embodiment, the data may also be used to compare with a threshold value and take a predefined action based on the comparison. The data may be received, collected, reviewed, and utilized using different forms of computer devices such as the portable electronic device 120.

In an implementation, the wearable sensor devices 102 may use the transceiver 112 to connect to and transfer data from the wearable sensor devices 102 to a local computer, and/or remote computer, and/or monitoring computer using one or more protocols. In an implementation, the wearable sensor devices 102 may use cellular, WIFI, radio frequency, and/or other forms of wireless (or wired) communication to transfer data. The transceiver 112 may transmit data via a processor capable of transmitting wireless and/or wired communication. Some examples of protocols which may be used to transfer data include ZigBee, WIFI, WiMAX, Bluetooth, Bluetooth Low Energy (BLE), or other over-the-air protocols. In an implementation, the transceiver 112 may transmit data via a satellite communication processor that is embedded with the wearable sensor device 102 and communication between the wearable sensor device 102 and a satellite may be established using a protocol compatible with the satellite.

In an implementation, the wearable sensor devices 102 may communicate using a variety of protocols and/or associated hardware devices or may switch from one form of communication to another in view of various factors including environment, cost, efficiency, etc. Suppose that a user of the wearable sensor device 102 is located outdoors in an environment where cellular, satellite, etc., communications are available. The wearable sensor device 102 may transmit data to a computer via one of the available communication methods. If, however, the user moves indoors, the wearable sensor device 102 may switch over to WIFI communications as a home WIFI device may be available to allow transmission of the data from the wearable sensor device 102 to a computer. In yet another implementation, suppose that one form of communication is weak (or expensive or less efficient than others), the wearable sensor device 102 may switch to another form of communication and transmit data accordingly.

The wearable sensor device 102 may further include a pre-filter 116 to reduce the amount of data that may be transfer from the wearable sensor device 102 to local computer (e.g., the portable electronic device 120), remote computer (408, as depicted in FIG. 4), and/or monitoring computer (406, as depicted in FIG. 4). The pre-filter 116 may be implemented in hardware, software, or combination of both. In one implementation, the pre-filter 116 may include one or more finite impulse response filter (not depicted), a memory (not depicted) and/or a processor (not depicted). In one implementation, the pre-filter 116 may operatively connected to the processor 104, the accelerometer 106, the memory 108, and/or the transceiver 112. In one implementation, the pre-filter 116 may be software instructions stored on the memory 108 and running on the processor 104. The pre-filter 116 may receive data from the accelerometer 106 or the memory 108. In one implementation, the pre-filter 116 may store an output from the pre-filter 116 to the memory 108. In another implementation, an output from the pre-filter 116 may be transmitted to the transceiver 112. The transceiver 112 may connect with and transfer the output outside of the wearable sensor device 102 (e.g., transfer the output to the portable electronic device 120). In one implementation, the pre-filter 116 is operatively connected to the accelerometer 106, and/or the transceiver 112 via wires (bus), wireless, and/or any form of communication known in the art.

In one implementation, the pre-filter 116 may include a low pass filter 118, a first buffer 140, a second buffer 122, and a measuring device 130. The measuring device 130 may further include a high threshold detector 124, a low threshold detector 126, and a flag 128. The components depicted within the pre-filter 116 may be internal to the pre-filter (as depicted) or in other implementations, the components may be external to the pre-filter and communicate with the pre-filter. Although a single pre-filter is depicted, in other implementations, multiple pre-filters may be utilized.

In an implementation, the system depicted in FIG. 2 provides transmission of data from the wearable sensor device 102 to the portable electronic device 120. As described above, the wearable sensor device 102 includes the pre-filter 116, an accelerometer 106, and a transmitter (part of device transceiver 112). The transmitter may communicate with the portable electronic device 120. Further, as described above with respect to FIG. 2, the pre-filter 116 includes the first buffer 140, the second buffer 122, the low pass filter 118, and the measuring device 130. The data may be used in order to detect a fall or train the neural network. Details regarding the pre-filter 116 and the neural network are described herein below.

A neural network may be initially trained (i.e., prior to detecting a fall) in order to appropriately detect a fall. Training may include providing various information in the form of data into the neural network before the actual usage. Details regarding the neural network are described herein below with respect to FIG. 5 and details regarding the training are described herein below.

In another implementation, as described above, the wearable sensor device 102 includes the pre-filter 116, the accelerometer 106, and the transmitter (part of transceiver 112). The pre-filter includes the first buffer 140, the second buffer 122, the low pass filter 118, the flag 128, and the low threshold detector 126. In the depicted implementation, the measuring device 130 includes the low threshold detector 126, the high threshold detector 124, and the flag 128. However, in other implementations, the low threshold detector 126, the high threshold detector 124, and/or the flag 128 may be external to the measuring device 130 and communicate with the measuring device 130.

Figure 3:
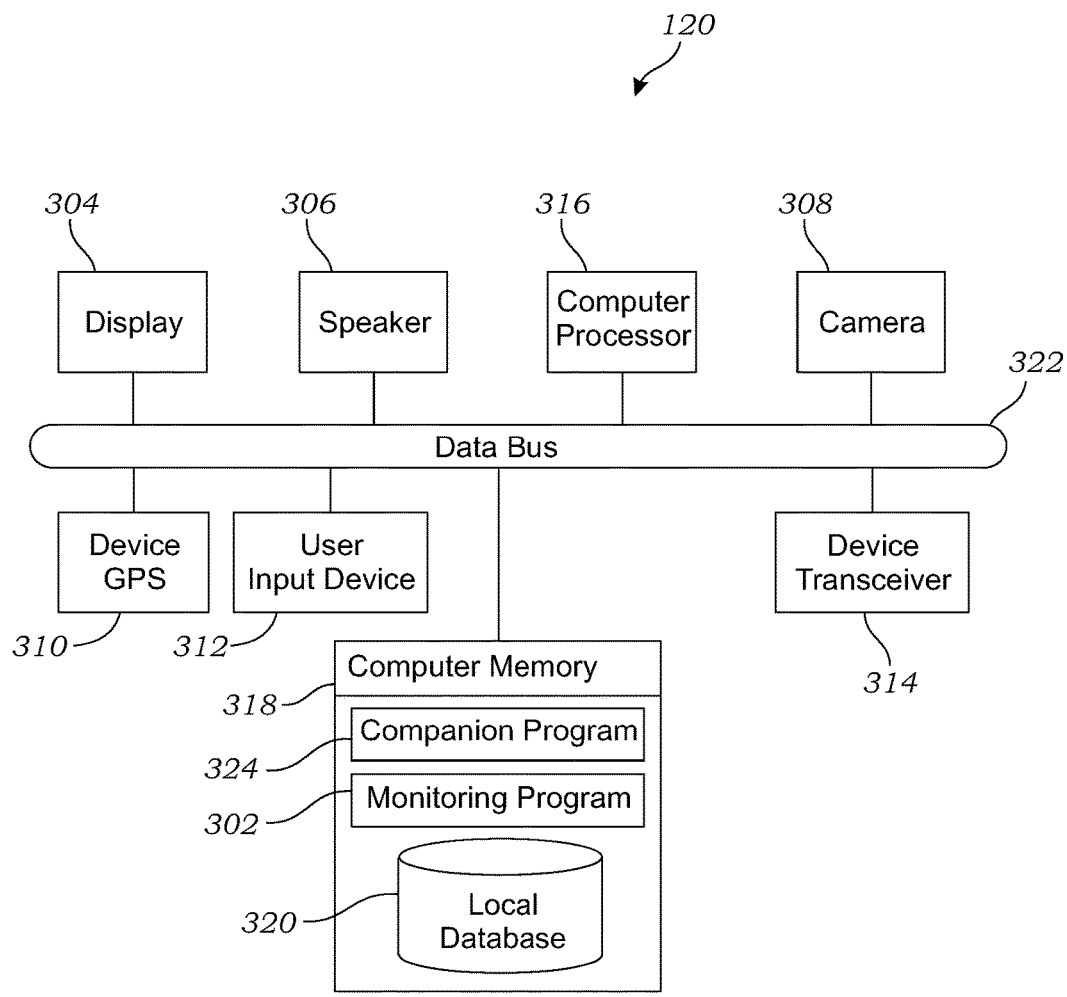
FIG. 3 is a block diagram of operable components of the portable electronic device of FIG. 1, according to one embodiment of the present invention.

FIG. 3 is a block diagram of operable components of the portable electronic device 120 of FIG. 1, according to one embodiment of the present invention. The portable electronic device 120 of this embodiment is a smart phone that includes a monitoring app 302 installed thereupon. The application, or "app," is a computer program that may be downloaded and installed using methods known in the art. The app enables the user to monitor their movement as detected and analyzed by the wearable sensor devices 102 and to communicate with the portable electronic device 120 to aid in executing proper physical motions. In the discussion of FIG. 3, we will begin with a description of the components of the portable electronic device 120, as they relate to the present invention. Then we will discuss in greater detail the functionality of the monitoring app 302, in one example, an embodiment used for physical therapy, and in another example, an embodiment for being used by a user performing a physical activity.

The portable electronic device 120 may include various electronic components known in the art for this type of device. In this embodiment, the portable electronic device 120 may include a device display 304, a speaker 306, a camera 308, a device global positioning system ("GPS") 310, a user input device 312 (e.g., touch screen, keyboard, microphone, and/or other form of input device known in the art), a user output device (such as earbuds, external speakers, and/or other form of output device known in the art), a device transceiver 314 for wireless communication, a computer processor 316, a computer memory 318, a monitoring app 302 operably installed in the computer memory 318, a local database 320 also installed in the computer memory 318, and a data bus 322 interconnecting the aforementioned components. For purposes of this application, the term "transceiver" is defined to include any form of transmitter and/or receiver known in the art, for cellular, WIFI, radio, and/or other form of wireless (or wired) communication known in the art. Obviously, these elements may vary, or may include alternatives known in the art, and such alternative embodiments should be considered within the scope of the claimed invention.

As shown in FIG. 3, the speaker 306 is typically integrated into the portable electronic device 120, although the speaker 306 may also be an external speaker. The speaker 306 may be used to give the user audio feedback and instructions to the user during use of the system, such as while exercising, etc. The speaker 306 may be any sort of speaker, known by those skilled in the art, capable of transforming electrical signals to auditory output.

In some embodiments, the monitoring app 302 monitors a user performing a physical activity such as walking, or any forms of stretches, exercises, rehabilitation routines, etc., and displays the physical activity in real time on the display 304 (defined to include near-real time, with a slight delay for computer processing, transmission, etc.). This display may be used to provide feedback to assist the user in performing the exercises correctly, and to provide encouragement to perform them as fully and correctly as possible.

The monitoring app 302 operably installed on the portable electronic device 120 may perform multiple tasks. In one example, a digital model (not shown) of the user may be generated and displayed on the computer display 304 of the portable electronic device 120. Movement of the digital model may be displayed, in real time, based upon the data received from the accelerometer 106, so that the digital model of the user approximates the movement of the user performing the physical activity.

This enables the user to watch himself/herself performing the physical activity, to better determine whether they are being performed correctly. The display may also be transmitted to other computer devices, such as a doctor, trainer, caretaker, etc., so that they may monitor the activities and take corrective action if required.

The movement of the digital model may also be compared with a preferred movement model of the monitoring app 302, to determine if the actual movement of the user approximates the preferred movement model, or if correction is needed. Communication with the user, in real time, with corrective instructions may be provided when correction is needed. Corrective instructions may include audio, text, video (e.g., video of the exercise being correctly performed), haptic, and/or any other medium desired to assist the user in performing the exercises such as running (or other activities) correctly.

Another synergistic use of the monitoring app 302 with common portable electronic device 120 is that the monitoring app 302 may be continuously calibrated by using the camera 308 of the portable electronic device 120 and common motion capture software. In this instance, if the motion capture determined that both the user's feet were on the ground, but for some reason the monitoring app 302 reported that the user's feet were not at the same level, the position of the user's feet in the monitoring app 302 could be reset to the correct value.

The integration of the device GPS 310 and the wearable sensor devices 102 provides several benefits. First, it may be another potential method of calibration. For example, if the net horizontal motion of the sensor devices 102, measured by the accelerometers 106, leads to the determination that the user has travelled a certain distance, this determination can be checked against the device GPS 310, and changes can be made to the data or the real-time acquisition programs to calibrate the system. The onboard device GPS 310 also increases the safety of the user. If the user was undergoing a strenuous activity and suddenly, and/or for an extended period of time, stopped, the monitoring app 302 may determine that a problem has occurred. The monitoring app 302 could then alert the authorities or others and provide the user's location.

There are many types of user input devices 312 that may be combined for use with the present invention. One type may be the touch-screen capability present in modern smartphones. Here, the user could adjust settings, program routines, select exercises, etc. Various user input devices 312 which may be integrated with present invention, for interfacing with the monitoring app 302 or the wearable sensor devices 102, should be considered equivalent and within the scope thereof.

The user output devices may be speakers, earbuds, external connections to computers, etc. The user output device is a key component of providing feedback to the user and/or others, who may be monitoring the user. Various user output devices may be integrated with present invention and should be considered equivalent and within the scope thereof.

The device transceiver 314 may be an integrated wireless transmitter/receiver combination, though a wired connection may be possible or desired in some instances. The device transceiver 314 may be used to communicate with the transceiver 112 on the wearable sensor devices 102, and/or other computers or monitoring devices. Such transceivers are known to those ordinarily skilled in the art and their equivalents should be considered within the scope of the present invention.

The local database 320 may be included for receiving and storing data temporarily, such as medical programs, therapy routines, logs from earlier use, a physical activity database including a different labeled sets of predefined physical activity patterns, where each such set corresponds to a physical activity, predefined time thresholds, predefined acceleration data thresholds, and information about the user; however, this is not required, and all data may be retained in another location if desired.

The above components may be interconnected via the data bus 322, which is a generic term for a conduit of information or electronic signals. There are many possible implementations of the data bus 322 by those ordinarily skilled in the art, and such implementations should be considered equivalent and within the scope of the present invention.

As illustrated in FIG. 3, the computer memory 318 of the portable electronic device 120 may be used to extend the utility of the portable electronic device 120. In this case, the computer memory of the portable electronic device 120 receives the monitoring app 302 and/or an internet browser for browsing web pages that may include additional medical or training programs. Additional programs may also be included, such as medical diagnostic programs, exercise routines, therapy routines, training programs, and others, some of which are discussed in greater detail below.

We begin a discussion of alternate embodiments of the present invention, by introducing an embodiment where the monitoring app 302 verifies connectivity with the transceiver 112 of the wearable sensor devices 102 and the device transceiver 314. In this embodiment, the monitoring app 302 continually monitors the acquisition of data. Should data acquisition be interrupted, the monitoring app 302 will make a predetermined number of attempts, three for example, to regain connectivity. Should this fail, an alarm or other visual, haptic, or audio cue will be produced, alerting the user to move the portable electronic device 120 closer to the wearable sensor devices 102 in order to regain the data connection.

In the embodiment of FIG. 3, the monitoring app 302 may be used to generate a graphical user interface on the device display 304 of the portable electronic device 120 to enable the user to interact with the monitoring app 302. In this embodiment, the graphical user interface may be used to show the user the position of their body, in two or three dimensions, while they are performing the actions required by the instruction program. Also, such instruction may be in the form of audio commands from the speaker 306, visual cues on the monitor of the portable electronic device 120, beeping or other audio cues from the speaker 306 that would indicate pacing or other information, or vibration of the portable electronic device 120. The information given to the user by the monitoring app 302 need not be just instruction, but could also indicate when to start or stop an activity, audio or visual feedback of the results of a completed activity, information on suggested future activities or programs to utilize, or trends of a user's progress in performing various activities.

With the acceleration data received from the accelerometer 106, the monitoring app 302 may guide the user as they perform the activity, and reconstruct their motion as it is saved in the computer memory 318. The monitoring app 302 may also provide feedback and encouragement to the user, telling them how to better perform the activity, giving them the time remaining, or coaxing them to continue even if the monitoring app 302 determines they are becoming fatigued.

In physical therapy it is just as important to not perform an activity incorrectly as it is to perform it correctly. Learning an incorrect way to move may slow the healing process, or even further injure the user. By monitoring the user's motions, the monitoring app 302 can instruct the user to stop if they are performing an activity too wrong, and if the problem cannot be corrected by the feedback provided, to seek the assistance of a medical practitioner before resuming exercises.

In a related embodiment, a companion app 324 may be installed on another instance of the portable electronic device 120, for providing a convenient way of monitoring a patient or user who is using the monitoring app 302, for example a doctor or nurse with the companion app 324 installed on a mobile device, such as a cell phone, laptop computer, tablet computer, etc. The companion app 324 may include the following functionality: the ability to report notifications of the physical activity status and acceleration data, as with the monitoring app 302, the ability to receive text, SMS, or other types of instant messaging or alerts to inform the user of the companion app 324 that the user of the monitoring app 302 has missed an exercise or other scheduled activity such as running, the ability to video the patient performing exercises, with the videos able to be sent to health care providers or others, and the ability to receive notifications from providers or others requesting videos or other data from the patient, practitioner, trainer, or any user of the companion app 324 or monitoring app 302. Other functions of the companion app 324 and their modes of implementation may be added or modified by those skilled in the art, and should be considered equivalent and within the scope of the present invention.

With the monitoring app 302 connected to a network (shown in FIG. 4), the data may be monitored in real-time or afterwards by medical practitioners or others. This has the potential for not just the sharing of information with numerous practitioners, but also the monitoring of the user's progress when not on-site, such as therapy performed in the user's home or other location away from the treatment facility.

In yet another embodiment, the monitoring app 302 may contain a mode wherein the monitoring app 302 instructs the accelerometer 106 to turn on for only brief periods of time during a longer duration exercise such as running a marathon. This allows data on the user's performance to be sampled throughout the duration of their activity, without the risk of draining the battery 110 as may happen for activities of long duration. Typically, the user has entered in the monitoring app 302 an estimate of the duration of their activity, usually measured in hours or fractions thereof.

In yet another embodiment, the monitoring app 302 may contain a mode useful for acquiring data for the user performing a physical activity. In one embodiment, the monitoring app 302 signals the user to begin running. In the case of sprinting, there is a time lag between the start of running and the attainment of the rhythmic full speed run. This occurs when the user is accelerating, getting their stride, etc. To save on memory space, data for some predetermined interval, for example two seconds, is not taken. After the two second delay, data is taken normally and throughout the end of the run. Optionally, data may be taken the entire time in order to capture the start as well, as feedback during that phase may be important to the user's performance. Also, if the user is primarily concerned with monitoring starts, the monitoring app 302 may only run for the first few seconds to record just that portion of the run.

The applications of the present invention go far beyond physical therapy. For instance the wearable sensor devices 102 may be used in the training of an athlete such as a martial artist, runner, or bicyclist. Here, the training is very similar to physical therapy, where technique can be monitored with feedback provided to the user and/or trainers. Also a history of the user's progress may be formed for use in charting progress and suggestions for further development.

FIG. 4 is a block diagram of one embodiment of the fall detection system 10 that includes the portable electronic device 120, a monitoring computer 406, and a remote computer 408 for monitoring the wearable sensor devices 102 and storing data. The wearable sensor devices 102, in the present embodiment, are operably connected (e.g., wirelessly) to the portable electronic device 120, such as via BLUETOOTH® or similar protocol.

In this embodiment, wherein the portable electronic device 120 is a cellular telephone, the portable electronic device 120 also streams data via a cellular network 402 (and/or another network 404, such as the Internet, or any form of local area network ("LAN") or a wireless network, to the other computers 406 and/or 408. Alternatively, in another embodiment, the portable electronic device 120 may communicate with the network 404 through a network device 410 such as a wireless transceiver or router. Here we consider two computers in the present embodiment of the invention, the remote computer 408 and the monitoring computer 406.

The remote computer 408 has a computer processor 412, a computer memory 414, a user interface 416 operably installed in the computer memory 414, a database 420 operably installed in the computer memory 414, and a remote display 418. The remote computer 408 functions primarily as a repository of data taken during the user's activity such as running. Data stored on the remote computer 408 may be accessed via the network 404 by other computers, or viewed locally using the remote display 418.

The monitoring computer 406 has a computer processor 422, a computer memory 424, a browser 426 operably installed in the computer memory 424, and a monitoring program 428 operably installed in the computer memory 424. Also, the computer may be connected to a monitoring display 430 for viewing the data and/or the output of the monitoring program 428, and have a printer 432 for printing physical copies of the same. The browser 426 may be a typical internet browser or other graphical user interface ("GUI") that may allow communication over the internet to the patient, other health care practitioners, or trainers. The monitoring program 428 interprets the results of the data sent by the monitoring app 302 and provides analysis and reports to the user of the monitoring computer 406. The monitoring program 428 provides information not included in the monitoring app 302, for example diagnosis of conditions and suggestions for treatment, or comparison of results with other patients either in real-time or by accessing the database 420 of the remote computer 408.

One embodiment of the fall detection system 10 includes providing the various components, particularly the accelerometer 106 in the wearable sensor devices 102, a unique address programmed therein for identification. The fall detection system 10 includes a data collection system 440 for simultaneously monitoring both the first and second locations and, in addition to any other number of locations that may be desired, around the world.

In this embodiment, the data collection system 440 may include a cell phone, and the remote computer 408 for simultaneously monitoring both the first location and a second location. In alternative embodiment, any one of these elements, or combinations thereof, may be used, in addition to any additional computer devices for tracking the data.

In this embodiment, a unique address is stored in each of the various components, and may include an IP address, or any form of unique indicator (e.g., alphanumeric). The address may be stored in the memory 424, or in any other hardware known in the art, and is transmitted with the data so that the data may be associated with the data in a database (e.g., the local database 320 of the portable electronic device 120, or the database 420 of the remote computer 408).

Data from the various components may then be streamed to the remote computer 408 (or other component of the data collection system 440) for storage in the database 420. For purposes of this application, "streaming data" may be performed in real time, with data being constantly transmitted (e.g., in typical "packets"), or it may be aggregated and sent periodically, or it may be stored and periodically downloaded (e.g., via USB or other connection) and transmitted.

In one embodiment, the data may include acceleration data from the accelerometer 106. Selected data, such as the acceleration data, may be transmitted in real time, while more complex data, such as the movement data may be stored in the memory 108 until a suitable trigger, such as actuation of a pushbutton, passage of a predetermined period of time, or other trigger (e.g., at the end of an exercise), and then streamed as a single transmission. Transmitting the data in this manner has proven to greatly relieve demands on the wearable sensor devices 102, which might otherwise make management of the data extremely difficult, especially when large numbers of users are utilizing the system.

In one embodiment, the data may be periodically analyzed by the remote computer 408 (or other suitable computer system) for "alarm conditions" (e.g., information and/or deviations that may be of interest to the user and/or the doctor and/or any other form of administrator). If an alarm condition is detected, a pertinent alert may be sent to the monitoring computer 406, directly to the user (e.g., via text message, email, signal to the portable electronic device 120, etc.), or to any other suitable party. For example, if the user is putting too much force on an injured leg during rehabilitation, or performing the exercise incorrectly, an alert may be sent to the user for immediate action, and/or a message (e.g., training video, etc.) may be sent via email or other method to help the user perform the exercise correctly.

Figure 5:
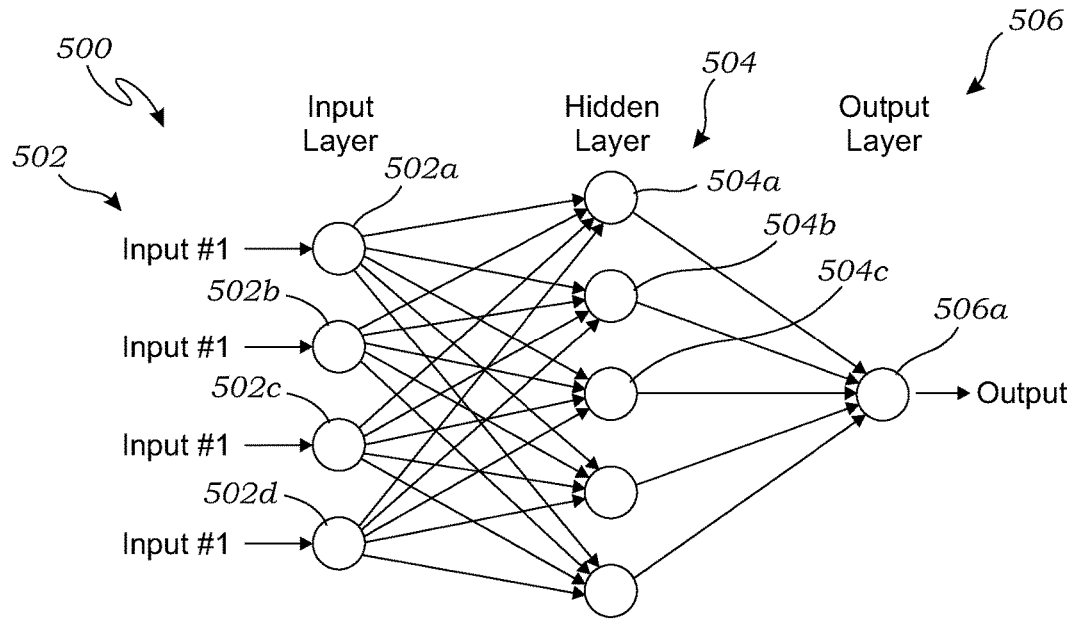
FIG. 5 is a diagram of a neural network utilized in the present embodiment of the fall detection system.
Figure 6:
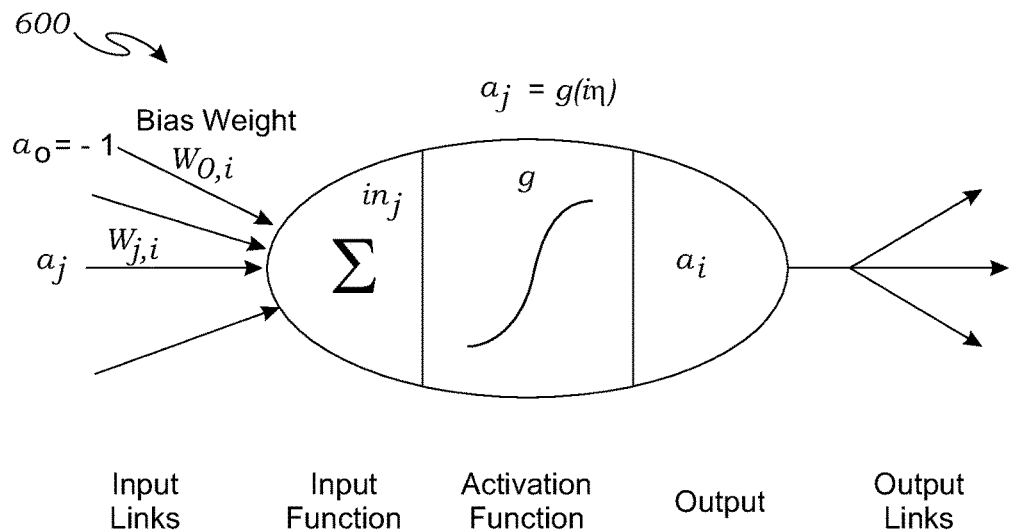
FIG. 6 is a diagram of an artificial neuron used in the neural network of FIG. 5.
Figure 7:
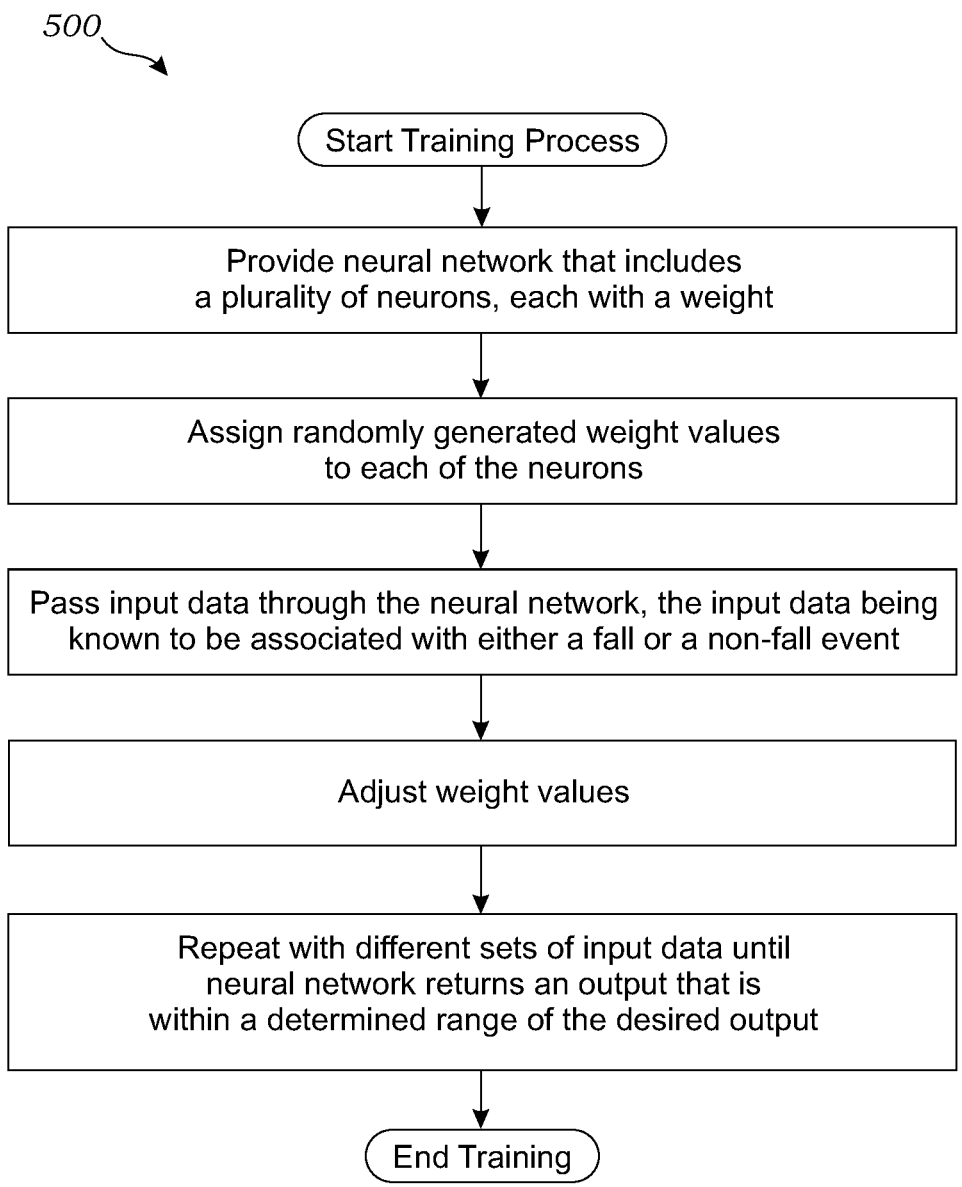
FIG. 7 is a flow diagram illustrating an exemplary method for training the neural network of FIG. 5.

Neural Network:

In a preferred embodiment of the present invention, the process of detecting a fall via the data from the wearable sensor device 102 (of FIG. 1) is performed by a neural network that is particularly adapted for this process. FIG. 5 is a diagram of one embodiment of a neural network 500 utilized in the present embodiment of the fall detection system 10 of FIG. 1. FIG. 6 is a diagram of an artificial neuron 600 used in the neural network of FIG. 5. FIG. 7 is a flow diagram illustrating an exemplary method for training the neural network 500 of FIG. 5.

In one embodiment, as shown in FIG. 5, an analysis of data from the sensor device of FIG. 1 may be performed via the neural network 500. As shown in FIG. 5, in this embodiment the neural network 500 comprises a large number of interconnected nodes in the form of artificial neurons, which are separated into different layers, and the connections between the nodes are characterized by associated weights. Each node has an associated function, one embodiment of which is shown in FIG. 6, causing it to generate an output dependent on the signals received on each input connection and the weights of those connections. The neural network 500 of FIG. 5 may be adaptive, in that the connection weights can be adjusted to change the response of the network to a particular input or class of inputs.

In the embodiment of FIG. 5, the neural network 500 comprises an input layer 502, a hidden layer 504 (which may include one or more layers), and an output layer 506. Each layer consists of nodes referred to as artificial neurons, i.e., artificial neurons 502a, 502b, 502c, and 502d of the input layer 502; and similarly, artificial neurons 504a, 504b, 504c, etc., of the hidden layer 504, and artificial neuron 506a of the output layer 506.

Each neuron may be connected all of the neurons in the adjacent layers. In this embodiment, each of the neurons of input layer 502 are connected to each of the neurons of hidden layer 504, and each of the neurons of hidden layer 506 are connected each of the neurons of output layer 506. Each of the connections between neurons in successive pairs of layers has an associated weight held in a matrix, and the number of layers and nodes is typically selected or adjusted according to the application the neural network 500 is intended to perform.

The neural network is adapted to be trained by using a training set comprising a set of inputs and corresponding expected outputs. The training tunes the network so that it performs well on the training set and, importantly, to generalize to untrained 'test' data. To achieve this, an error signal is generated from the difference between the expected output and the actual output of the network, and a summary of the error called the loss or cost is computed (e.g., the sum of squared errors).

Back-propagation of error may be used to compute the precise gradient of the loss with respect to the network weights. This gradient is used as a training signal and is generated from the forward connection weights and error signal and fed back to modify the forward connection weights. Back-propagation thus requires that error be fed back through the network via a pathway which depends explicitly and intricately on the forward connections. This requirement of a strict match between the forward path and feedback path is problematic for a number of reasons. One issue which arises when training deep networks is the 'vanishing gradient' problem where the backward path tends to shrink the error gradients and thus make very small updates to neurons in deeper layers which prevents effective learning in such deeper networks.

In some embodiments, the neural network may include more than one hidden layer. The errors in the back-propagation may be transmitted to the deeper layers in a stepwise manner. In networks with 1 or 2 hidden layers, it is simple to manually select (e.g. by trial and error) a scale for the feedback matrices which produces good learning results. In networks with many hidden layers, it may be helpful to choose the scale of the feedback matrices more carefully so that error flows back to the deep layers without becoming too small (i.e. 'vanishing') or becoming too large (i.e. 'exploding').

The inputs are then multiplied with a weight (every single input in the entire neural network will have its own weight connected to it) then they are all added together with the bias (the bias also has a connected weight). The bias is there to determine how significant each individual neuron is. The bias value is always one, but the connected weight can differ.

Once the values are summed together, they are passed through a transfer function. We are using a sigmoid function for this.

The output value generated by the sigmoid function will always be between 0 and 1. This is the output value from the neuron, which is then connected to neurons in the next layer, or if this is a neuron in the output layer, it would be the neural network output. The final output will also be between 0 and 1, where 0.99 would be 99% chance for fall and 0.22 would be 22% chance for fall. We then decide how sensitive we want the algorithm to be (how high of a percentage would we need in the output to alert the user of a fall).

There are many things a neural network can learn, what makes them unique is the structure (how many neurons in each layer, how many layers etc.), the weights, and the input. A small network will be faster to train, but will not be able to learn as complex concepts as larger networks. The weights are what we are going to train/change. By having the correct weight values, the neural network should be able to differ between fall and non-fall input data.

Inputs:

The fall detection algorithm uses data from the accelerometers in the sensor device(s) of FIG. 1, in this case in the form of an armband. The armband of this embodiment provides x, z and y values every 100 ms (this interval can be adjusted if needed). We use these values to calculate a vector of acceleration.

In this embodiment, once a certain number of vectors are received, in this case 120 vectors, the vectors are averaged by adding together 60% of the most recent vector, 25% of the vector before, and 15% of the one before that again. This gives us a total of 40 inputs for our network. The math and number of vectors/inputs can be adjusted to optimize the algorithm.

Pre-Filter:

A pre-filter is designed to reduce the amount of data passed through the neural network by eliminating data sets which are mathematically proven not to be likely falls. Eliminating data sets may be performed by analyzing the data using the following formula:

X: the set of data points in a particular pattern(fall/non-fallcase)

min(X): the minimum value in the set X max(X): the maximum value in the set X y=max(X)−min(X)

After the pre-filter processes the above formula, determining whether a jerk value is higher or lower than a pre-determined value may be implemented by the pre-filter to further reduce the amount of data to be processed. Jerk, also known as jolt, surge, or lurch, is a rate of change of acceleration; that is, the derivative of acceleration with respect to time, and as such, the second derivative of velocity, or the third derivative of position. Jerk is a vector, and there is no generally used term to describe its scalar magnitude (more precisely, its norm, e.g. 'speed' as the norm of the velocity vector).

The pre-filter provides data to a neural network, which can detect a fall. In an implementation, the neural network may reside within the wearable sensor device 102. In other implementations, the neural network may reside elsewhere. Details regarding the pre-filter providing data to a neural network are described herein with respect to FIG. 8.

Figure 8:
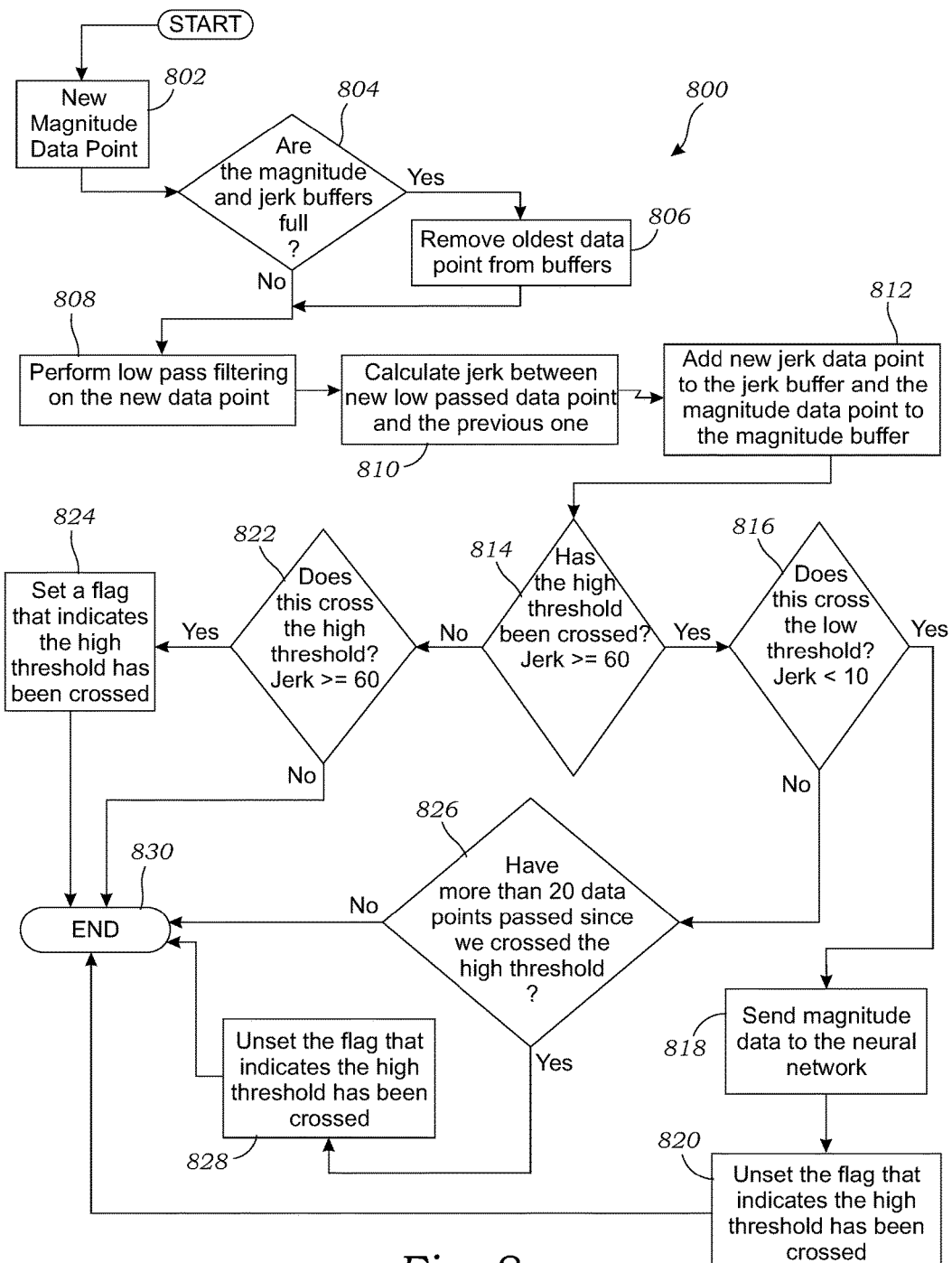
FIG. 8 is a flowchart illustrating an exemplary method of providing data to a neural network, according to one embodiment of the present invention.

FIG. 8 is a flowchart illustrating an exemplary method 800 of providing data to a neural network. Method 800 may be performed by a pre-filter that may include hardware (e.g., circuitry, dedicated logic, programmable logic, microcode, etc.), software (e.g., instructions run on a processing device to perform hardware simulation), or a combination there of. In one implementation, the pre-filter may include a measuring device that may further include a low pass filter (e.g., finite impulse response filter, etc.). The pre-filter may include one or more buffers to store data. The pre-filter used to perform method 800 is described in FIG. 2. Thus, the method of FIG. 8 may be performed by pre-filter 116 of FIG. 2 and components described in FIG. 2 may be referred to with respect to the steps described herein below in FIG. 8. The method of FIG. 8 is a flow diagram illustrating an efficient method of providing data to the neural network 500 of FIG. 5. The pre-filter may perform the steps described within the blocks depicted in FIG. 8.

Referring to FIG. 8, the method 800 begins at block 802 when a new magnitude data point is received at the pre-filter. Referring to FIG. 2, the accelerometer 106 may provide one or more magnitude data points on the linear acceleration: three linear dimensions (x, y and z axes), roll pitch, yaw, position, bearing, and heading. These nine coordinate measurements provide a complete description of the motion and position of the user, as measured via the accelerometer 106. In one implementation, the magnitude data point may be a value calculated with respect to a coordinate measurement received by the pre-filter 116 from accelerometer 106. For example, in one implementation, the magnitude data point may be a sum of square of three linear dimensions, calculated as follows:

$$M=x^2+y^2+z^2$$

The variable 'M' stands for a magnitude. The variables 'x', 'y', and 'z' are each axes of linear dimension with respect to the gravity of the earth due to the physical activity being performed by the user. In other implementations, other combination of measurements from the accelerometer may be used to calculate a magnitude data point.

Referring again to FIG. 8, at decision block 804, a determination is made whether both a buffer for magnitude data points and a buffer for jerk values are full. In one implementation, a jerk value may be calculated in relation to two separate magnitude data points. For example, the jerk value may be calculated by subtracting one magnitude data point from another and then dividing the result of that subtraction by time.

In response to decision block 804 returning a "yes," the method continues to block 806 where the oldest magnitude data point and jerk value are removed from the buffers. The method continues to block 808. The oldest magnitude data point and jerk values are the oldest data points (i.e., first in) in each buffer. For example, if the chronological order of magnitude data points in a buffer are magnitude data point 1, magnitude data point 2, and magnitude data point 3, where magnitude data point 1 is inserted into the buffer first followed by magnitude data point 2, and magnitude data point 3 is lastly inserted, then the oldest data point would be magnitude data point 1.

In response to decision block 804 return a "no," the method continues to block 808.

In block 808, low pass filtering is performed and the magnitude data point is passed to a low pass filter. The low pass filter may be a 3-tap filter. The "tap" value, for example, may be 0.030448, 0.939103, and 0.030448. The 3-tap filter may be a finite impulse response filter that is known.

In block 810, a jerk value is calculated in relation to the magnitude data point and the previous magnitude data point is received at the pre-filter. In one implementation, the previous magnitude data point may be, for example, the last magnitude point calculated and stored by the pre-filter before receiving the current magnitude data point.

In block 812, the jerk value is appended to a buffer and the magnitude data point is appended to another buffer (i.e., a second buffer) that is different from the buffer (i.e., the first buffer) where the jerk value is appended. Then, the method continues to block 814.

In one implementation, the pre-filter may include a flag to keep track of a state of a jerk value. The flag may be set in response to a certain state and unset in response to another state. In one implementation, a flag that has been set indicates that a jerk value is higher than a high threshold value. Referring back to FIG. 8, at decision block 814, a determination is made whether a high threshold has been met or crossed. In one implementation, the high threshold value may be sixty. In other implementations, the high threshold value may be another value.

In response to decision block 814 returning a "yes," the method continues to decision block 816. At decision block 816, a determination is made whether the jerk value is lower than/meets/crosses a low threshold value. In one implementation, the low threshold value may be ten. In other implementations, the low threshold value may be another value.

In response to decision block 816 returning a "yes," the method continues to block 818. In block 818, the magnitude data point is transmitted to the neural network and the method continues to block 820. The magnitude data point is described in block 802 in the above.

In block 820, the flag that indicates the high threshold has been crossed or met is unset. In other words, the flag returns to its originally unset state.

The method then ends at block 830.

In response to decision block 816 returning a "no," the method continues to decision block 826. At decision block 826, a determination is made whether the pre-filter has processed a predetermined number of jerk values. For example, in one implementation, processing of a jerk value by the pre-filter may include determining whether the jerk value reached a high or low threshold value. In the depicted implementation, it is determined whether more than twenty data points passed since the high threshold was crossed or met. In other implementations, any number of data points may be used.

In response to decision block 826 returning a "yes," the method continues to block 828. In block 828, the flag that indicates the high threshold has been crossed or met is unset and, then, the method ends at block 830.

In response to decision block 826 returning a "no", the method ends at block 830.

In response to decision block 814 returning "no," the method continues to decision block 822. At decision block 822, a determination is made whether the jerk value crosses/meets/is higher than the high threshold value. For example, the high threshold value may be sixty and it is determined at decision block 822 whether the jerk value is higher than sixty.

In response to decision block 822 returning "yes," the flag that indicates the high threshold has been crossed or met is set, at block 824, and, then, the method ends at block 830.

In response to decision block 822 turning "no," the method ends at block 830.

In an implementation, the values referenced in FIG. 8 are for exemplary purposes only and other values (not depicted) may be used.

In an embedded system such as the wearable sensor device 102 depicted in FIG. 2, the pre-filter filters streaming data and may be restricted to analyze each magnitude data point as it arrives substantially in real-time. For example, the accelerometer may determine/capture data that may be indicative or not of fall data in substantially real-time and stream it to the pre-filter. The restriction may be compensated by phasing. Phasing divides data into a pre-determined number of data sets. In one implementation, phasing may be used to provide data from the accelerometer to the pre-filter. In one implementation, five phases may be used and data may be divided into five data sets. For example, in one implementation of collecting data at 100 Hz via the accelerometer, one second of data is divided into five data sets as following:

Phase 1: data#1, data#6 . . .
Phase 2: data#2, data#7 . . .
Phase 3: data#3, data#8 . . .
Phase 4: data#4, data#9 . . .
Phase 5: data#5, data#10 . . .

Then, one phase at a time is transmitted and received at the pre-filter. In an implementation, a phase may be transmitted by a portion of the pre-filter, the accelerometer, or another entity (e.g., an entity that is in between the accelerometer and the pre-filter). In one implementation, training of a neural network may utilize all or more than one of the phases whereas during fall detection, fewer phases than used in training may be utilized. In the above example, during training of a neural network, all five phases may be transmitted to the pre-filter. During fall detection, one phase, which may be selected randomly or otherwise, may be transmitted to the pre-filter. Therefore, during fall detection, the pre-filter can utilize less data (less phases), thus, providing an efficient fall detection system.

Figure 9:
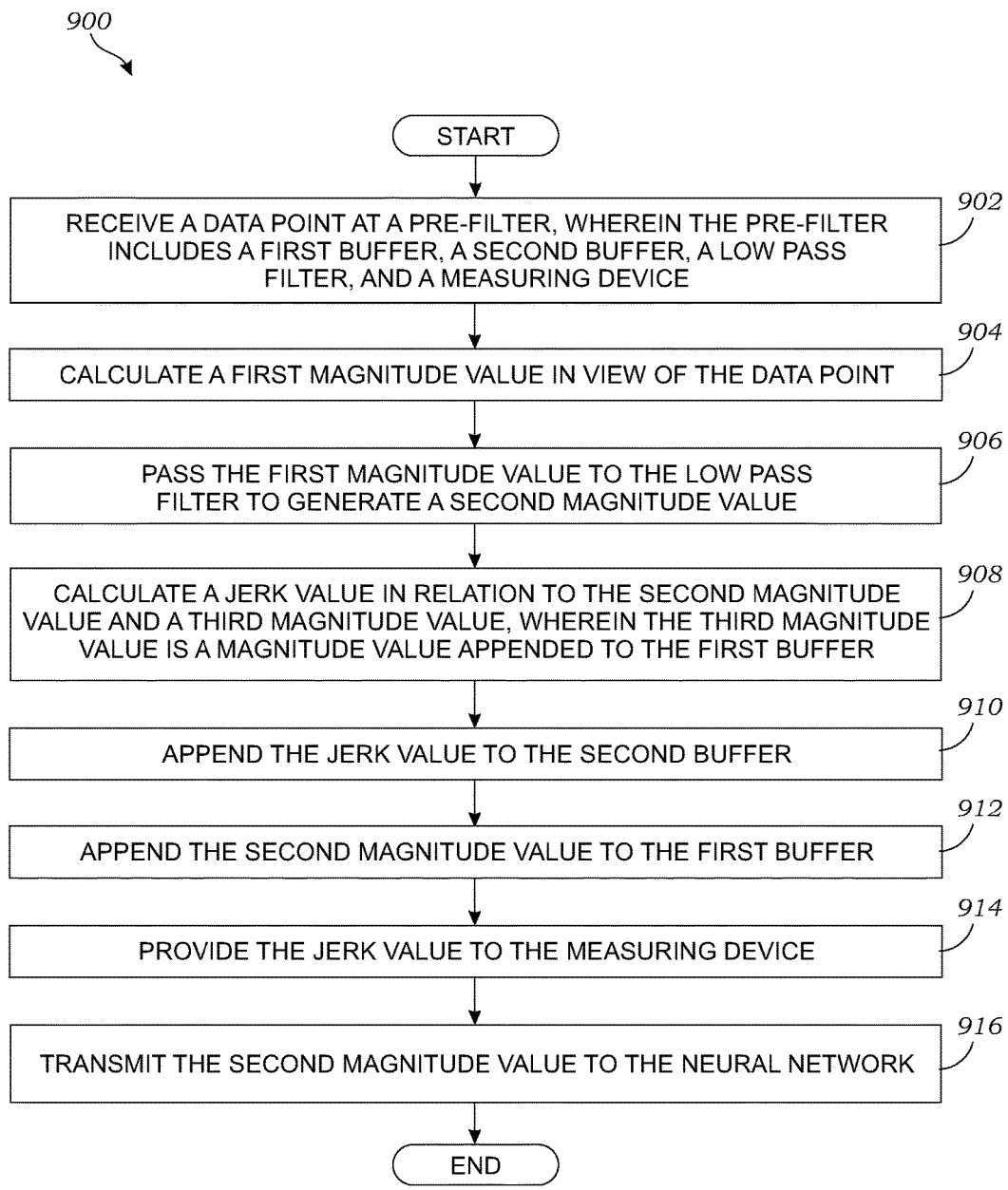
FIG. 9 is a flowchart of an exemplary method of providing data to a neural network for detecting a fall of person having a portable electronic device, according to one embodiment of the present invention.

FIG. 9 is a flowchart of an exemplary method 900 of providing data to a neural network for detecting a fall of person having a portable electronic device. Method 900 may be performed by a pre-filter that may include hardware (e.g., circuitry, dedicated logic, programmable logic, microcode, etc.), software (e.g., instructions run on a processing device to perform hardware simulation), or a combination there of. In one implementation, the pre-filter may include a low pass filter (e.g., finite impulse response filter), one or more buffers to store data, and a measuring device. The pre-filter used by method 900 is described in FIG. 2. The method of FIG. 9 may be performed by the pre-filter 116 of FIG. 2 and components described in FIG. 2 may be referred to with respect to the steps described herein below in FIG. 9.

Referring now to FIG. 9, at step 902, the pre-filter receives a data point. The pre-filter includes a first buffer, a second buffer, a low pass filter, and a measuring device. Referring to FIG. 2, the pre-filter 116 includes the first buffer 140, the second buffer 122, the low pass filter 118, and the measuring device 130. In an implementation, the accelerometer 106 transmits the data point to the pre-filter 116.

Referring again to FIG. 9, at step 904, the pre-filter calculates a first magnitude value in view of the data point. The first magnitude value may be calculated by sum of square of the data point as described above.

Referring again to FIG. 9, at step 906, the pre-filter passes the first magnitude value to the low pass filter to generate a second magnitude value. Referring to FIG. 2, the pre-filter 116 passes the first magnitude value to the low pass filter 118 to generate a second magnitude value. The second magnitude value is the first magnitude value passed via the low pass filter.

Referring again to FIG. 9, at step 908, the pre-filter calculates a jerk value in relation to the second magnitude value and a third magnitude value. The third magnitude value is a magnitude value the previous second magnitude value appended to the first buffer.

Referring again to FIG. 9, at step 910, the pre-filter appends the jerk value to the second buffer. As depicted in FIG. 8, at block 812, the pre-filter appends the jerk value to the second buffer. As depicted in FIG. 2, the pre-filter 116 appends the jerk value to the second buffer 122.

Referring again to FIG. 9, at step 912, the pre-filter appends the second magnitude value to the first buffer. As depicted in FIG. 8, at block 812, the pre-filter appends the second magnitude value to the first buffer. As depicted in FIG. 2, the pre-filter 116 appends the second magnitude value to the first buffer 140.

Referring again to FIG. 9, at step 914, the pre-filter provides the jerk value to the measuring device. As depicted in FIG. 2, the pre-filter 116 provides the jerk value to the measuring device 130.

Referring again to FIG. 9, at step 916, the pre-filter transmits the second magnitude value to the neural network.

Referring to FIG. 2, the pre-filter 116 transmits the second magnitude value the neural network 500, depicted in FIG. 5.

The method then ends.

In an implementation, the pre-filter includes a flag. As depicted in FIG. 2, the pre-filter 116 includes the measuring device 130 which includes the flag 128 and the high threshold detector 124. The pre-filter 116 in FIG. 2 sets the flag in response to the high threshold detector 124 detecting the jerk value meeting a high threshold. The high threshold is greater than or equal to a high threshold value.

In an implementation, when the flag is set, the pre-filter 116 passes the jerk value to the low threshold detector 126. The pre-filter also detects the jerk value meeting a low threshold. The low threshold is lower than a low threshold value. The pre-filter 116 also transmits the second magnitude to the neural network in response to the detecting of the jerk value meeting the low threshold.

In an implementation, the pre-filter includes a flag and as depicted in FIG. 2. In response to the following: the flag being set; meeting of the low threshold not being detected; and in response to greater than a predetermined number of data points being passed to the pre-filter since the flag was set, the pre-filter 116 unsets the flag. For example, in one implementation where the predetermined number of data has a value of twenty, in response to twenty first data point being passed to the pre-filter since the flag was set, the flag will be unset.

In an implementation, the third magnitude value described in step 908 of FIG. 9 is a last magnitude value appended to the first buffer.

Figure 10:
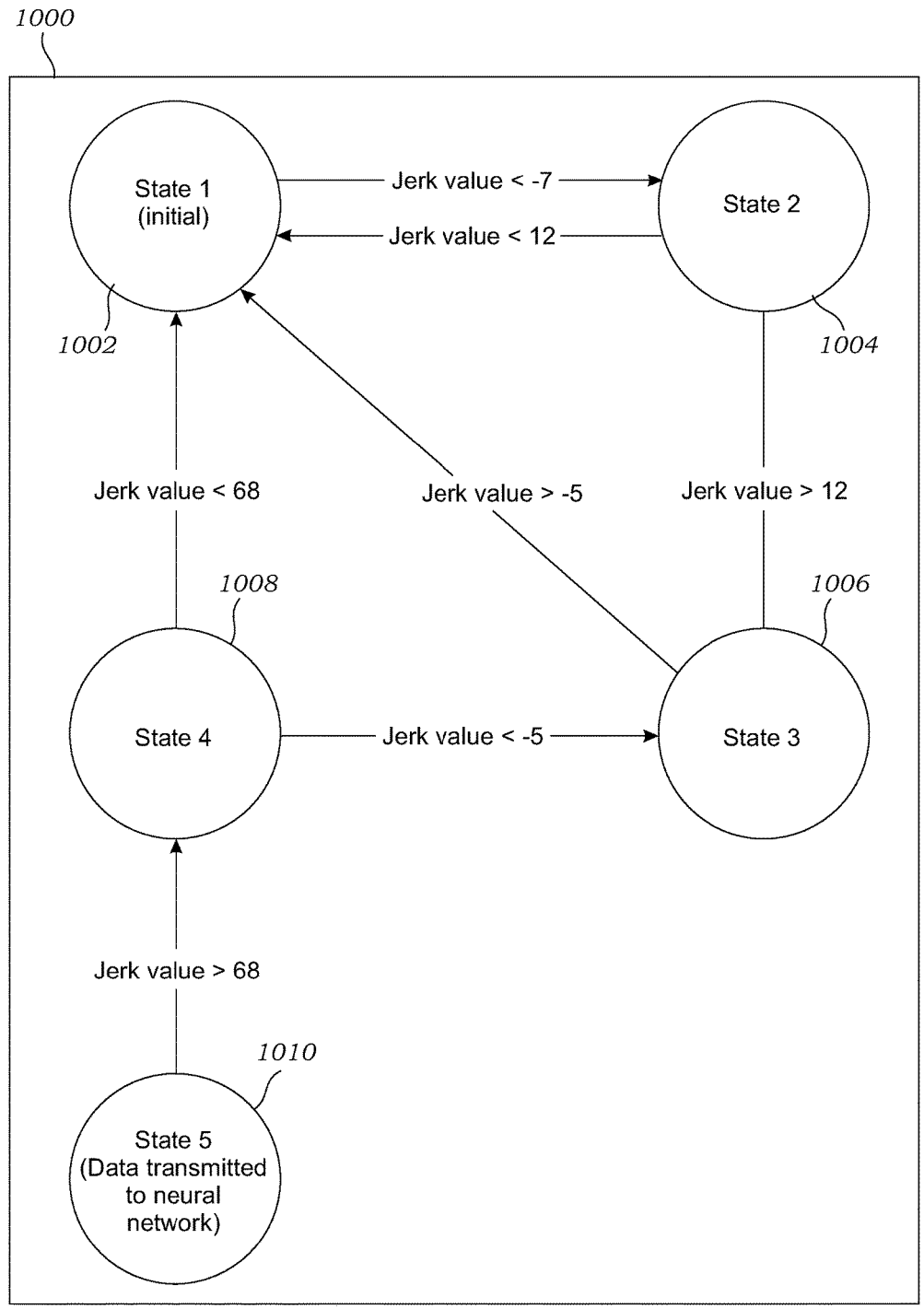
FIG. 10 is a flow diagram illustrating an efficient method of providing data to a neural network using a finite state machine, according to one embodiment of the present invention.

In another implementation, a finite state machine may be utilized to eliminate data by the pre-filter, where the data may be mathematically proven not to be likely falls. Therefore, by eliminating such data, an efficient system that utilizes fewer resources (i.e., less processing power, less hardware/software resources such as memory, etc.) to process the reduced data may result. The functionality of the finite state machine 1000 may be performed by a pre-filter that may include hardware (e.g., circuitry, dedicated logic, programmable logic, microcode, etc.), software (e.g., instructions run on a processing device to perform hardware simulation), or a combination there of. The functionality by the finite state machine 1000 may alternatively be performed elsewhere and communicated to the pre-filter. The finite state machine 100 may include hardware, software, or a combination thereof and may exist internal or external to the pre-filter. Detail regarding the pre-filter are described above in FIG. 2. Components described in FIG. 2 may be referred to with respect to the steps described herein below in FIG. 10. FIG. 10 is a flow diagram illustrating an efficient method of providing data to the neural network 500 of FIG. 5 using a finite state machine.

Referring to FIG. 10, the finite state machine begins at state 1 (1002) when it receives a jerk value. A method of obtaining the jerk value may be similar to the method described in FIG. 8, blocks 810 and 812. Referring back to FIG. 10, in response to the jerk value less than a value of −7, the finite state machine moves to the state 2 (1004) and waits for a next jerk value. The next jerk value is another data point received by the pre-filter 116 of FIG. 2, right after the current operation of the pre-filter 116 is performed.

Referring back to FIG. 10, in response to receiving the next jerk value greater than 12, the finite state machine moves to state 3 (1006). In response to the next jerk value being less than or equal to 12, the finite state machine returns to the initial state (state 1 (1002)) and waits for a next jerk value.

In response to receiving the next jerk value greater than −5, the finite state machine moves to state 4 (1008). In response to the next jerk value being less than or equal to −5, the finite state machine returns to the initial state (state 1 (1002)) and waits for a next jerk value.

In response to receiving the next jerk value greater than 68, the finite state machine moves to state 5 (1010), and the magnitude data point in FIG. 8, block 812 may be transmitted to the neural network. Thereafter, the finite state machine returns to the initial state (state 1 (1002)) and waits for a next jerk value. In response to the next jerk value being less than or equal to 68, the finite state machine returns to the initial state (state 1 (1002)) and waits for a next jerk value.

Training:

A backpropagation algorithm is used to train the weights in the current neural network. Input data (that we already know if it's a fall or not) is passed to the network (with randomly generated weight values). We then get an output from the network, that we can compare to our desired output (desired output for a fall would be 1, and non-fall would be 0).

In one embodiment, the training of the artificial neurons comprises the steps of: randomly generating the connection weights of the artificial neurons; passing a set of input data through the neural network, the input data being associated with fall events and non-fall events; adjusting the connection weights; and repeating with different sets of input data until the neural network returns an output that is within a determined range of a desired output.

There are two cases to consider when training weights in a neural network with backpropagation, weights in the output layer and weights in the hidden layer(s). To calculate what we should change the weight of an output layer, in this embodiment, we use the following formula:

$$\Delta W = \frac{\partial E}{\partial_k} = (O_k - t_k)O_k(1 - O_k)O_j$$

Here we are calculating the change in weight for the weight connecting node j in L−1 layer to node k in the L layer.

Ok—output for the neural network
Tk—target output
Oj—output from node j in the L−1 layer We can now change the weight to:

$$W+ = Wjk + (\Delta W^* \mu)$$

Where µ is the learning weight.

If the weight is in a hidden layer, we use the following:

$$\Delta W = \frac{\partial E}{\partial W_{ij}} = O_j(1 - O)_i \sum_{k \in K}(O_k - t_k)O_k(1 - O_k)W_{jk}$$

Once we have trained all of the weights in the network, we move over to a new set of training data, and train on these (until we have trained the network on all our desired training data). When you have trained the network on all training sets, start over and repeat until the output from all datasets are within a determined range of the desired output (this could take millions of passes before it occurs).

The computer or computers used in the personal monitoring system may be any form of computers or computers, servers, or networks known in the art. As used in this application, the terms computer, processor, memory, and other computer related components, are hereby expressly defined to include any arrangement of computer(s), processor(s), memory device or devices, and/or computer components, either as a single unit or operably connected and/or networked across multiple computers (or distributed computer components), to perform the functions described herein.

The exemplary embodiments described herein detail for illustrative purposes are subject to many variations of structure and design. It should be emphasized, however that the present invention is not limited to particular method of manufacturing wearable sensor devices as shown and described. Rather, the principles of the present invention can be used with a variety of methods of manufacturing wearable sensor devices. It is understood that various omissions, substitutions of equivalents are contemplated as circumstances may suggest or render expedient, but the present invention is intended to cover the application or implementation without departing from the spirit or scope of the claims.

As used in this application, the words "a," "an," and "one" are defined to include one or more of the referenced item unless specifically stated otherwise. Also, the terms "have," "include," "contain," and similar terms are defined to mean "comprising" unless specifically stated otherwise. The term 'shoes' or 'footwear' may have been used above interchangeably and refer to convey the same meaning. The term "activity" as used in this application refers to any activity that the user of the present invention may be undertaking, whether it is exercise, training, physical therapy, or routine activities. Also, pressure and force may be used interchangeably as pressure is simply a scalar quantity that relates the applied force to a known surface area. Furthermore, the terminology used in the specification provided above is hereby defined to include similar and/or equivalent terms, and/or alternative embodiments that would be considered obvious to one skilled in the art given the teachings of the present patent application.

What is claimed is:

1. A computer-implemented method for providing data to a neural network for detecting a fall of person having a portable electronic device, the method comprising the steps of:

phasing, via a processing device of a pre-filter, data points, wherein the phasing comprises dividing the data points into a predetermined number of data sets;

receiving a data point of the predetermined number of data sets at the processing device of the pre-filter, wherein the data point is selected for pre-filtering, and wherein the pre-filter comprises a first buffer, a second buffer, a low pass filter, and a measuring device;

calculating a first magnitude value in view of the data point;

passing the first magnitude value to the low pass filter to generate a second magnitude value;

calculating a jerk value in relation to the second magnitude value and a third magnitude value, wherein the third magnitude value is a magnitude value appended to the first buffer;

appending the jerk value to the second buffer;

appending the second magnitude value to the first buffer;

providing the jerk value to the measuring device; and transmitting the second magnitude value to the neural network.

2. The computer-implemented method of claim 1, wherein the pre-filter comprises a flag and wherein the measuring device comprises a high threshold detector, the method further comprising a step of:
   setting the flag in response to the high threshold detector detecting the jerk value meeting a high threshold, wherein the high threshold is greater than or equal to a predetermined value.

3. The computer-implemented method of claim 1, wherein the pre-filter comprises a flag and wherein the measuring device comprises a low threshold detector and when the flag is set, the method further comprising steps of:
   passing the jerk value to the low threshold detector;
   detecting the jerk value meeting a low threshold, wherein the low threshold is lower than a predetermined value; and
   transmitting the second magnitude value to the neural network in response to the detecting of the jerk value meeting the low threshold.

4. The computer-implemented method of claim 1, wherein the pre-filter comprises a flag and in response the flag being set, meeting of a low threshold not being detected, and in response to greater than a predetermined number of data points being passed to the pre-filter since the flag was set, the method further comprising a step of:
   unsetting the flag.

5. The computer-implemented method of claim 1, wherein the third magnitude value is a last magnitude value appended to the first buffer.

6. A system for providing data to a neural network, the system comprising:
   a wearable device comprising a pre-filter, an accelerometer and a transmitter configured to communicate with a portable electronic device, wherein the pre-filter comprises a first buffer, a second buffer, a low pass filter, and a measuring device, wherein the pre-filter is configured to:
      perform, via a processing device, phasing of data points, wherein the data points are transmitted by the accelerometer, and wherein the phasing comprises dividing data points into a predetermined number of data sets;
      receive a data point of the predetermined number of data sets, wherein the data point is selected for pre-filtering;
      calculate a first magnitude value in view of the data point;
      pass the first magnitude value to the low pass filter to generate a second magnitude value;
      calculate a jerk value in relation to the second magnitude value and a third magnitude value, wherein the third magnitude value is a magnitude value appended to the first buffer;
      append the jerk value to the second buffer;
      append the second magnitude value to the first buffer;
      provide the jerk value to the measuring device; and
      transmit the second magnitude value to the neural network.

7. The system of claim 6, wherein the pre-filter comprises a flag and wherein the measuring device comprises a high threshold detector, the pre-filter is configured to:
   set the flag in response to the high threshold detector detecting the jerk value meeting a high threshold, wherein the high threshold is greater than or equal to a predetermined value.

8. The system of claim 6, wherein the pre-filter comprises a flag and wherein the measuring device comprises a low threshold detector and when the flag is set, the pre-filter is configured to:
   pass the jerk value to the low threshold detector;
   detect the jerk value meeting a low threshold, wherein the low threshold is lower than a predetermined value; and
   transmit the second magnitude value to the neural network in response to detecting of the jerk value meeting the low threshold.

9. The system of claim 8, wherein the pre-filter sets the flag.

10. The system of claim 9, wherein the pre-filter is configured to unset the flag in response to:
   the low threshold detector not detecting the jerk value meeting the low threshold; and
   a predetermined number of data points being passed to the pre-filter since the flag was set.

11. A wearable device system comprising:
   a pre-filter;
   an accelerometer; and
   a transmitter configured to communicate with a portable electronic device, wherein the pre-filter comprises a first buffer, a second buffer, a low pass filter, a flag, and a low threshold detector, wherein the pre-filter is configured to:
      perform, via a processing device, phasing of data points, wherein the data points are transmitted by the accelerometer, and wherein the phasing comprises dividing data points into a predetermined number of data sets;
      receive a data point of the predetermined number of data sets, wherein the data point is selected for pre-filtering;
      calculate a first magnitude value in view of a data point;
      pass the first magnitude value to the low pass filter to generate a second magnitude value;
      calculate a jerk value in relation to the second magnitude value and a third magnitude value, wherein the third magnitude value is a magnitude value appended to the first buffer;
      append the jerk value to the second buffer;
      append the second magnitude value to the first buffer;
      provide the jerk value to the low threshold detector in response to the flag being set; and
      provide the second magnitude value to the transmitter in response to the low threshold detector detecting the jerk value meeting a low threshold, wherein the low threshold is lower than a predetermined value.

12. The wearable device system of claim 11, wherein the pre-filter further comprises a high threshold detector, the pre-filter is configured to:
   set the flag in response to the high threshold detector detecting the jerk value meeting a high threshold, wherein the high threshold is greater than or equal to a predetermined value.

13. The wearable device system of claim 11, wherein the pre-filter sets the flag.

14. The wearable device system of claim 13, wherein the pre-filter is configured to unset the flag in response to:
   the low threshold detector not detecting the jerk value meeting the low threshold; and
   a predetermined number of data points being passed to the pre-filter since the flag was set.

* * * * *